United States Patent [19]
Linden

[11] Patent Number: 6,117,878
[45] Date of Patent: Sep. 12, 2000

[54] 8-PHENYL- OR 8-CYCLOALKYL XANTHINE ANTAGONISTS OF A2B HUMAN ADENOSINE RECEPTORS

[75] Inventor: Joel M. Linden, Charlottesville, Va.

[73] Assignees: University of Virginia; University of Virginia Patent Foundation, both of Charlottesville, Va.

[21] Appl. No.: 09/027,649

[22] Filed: Feb. 24, 1998

[51] Int. Cl.[7] ................................................. A61K 31/52
[52] U.S. Cl. ............................................................ 514/263
[58] Field of Search ........................................... 514/263

[56] References Cited

U.S. PATENT DOCUMENTS

| | | | |
|---|---|---|---|
| 4,193,926 | 3/1980 | Schmiechen et al. | 260/326 |
| 4,824,660 | 4/1989 | Angello et al. | 424/1.1 |
| 4,938,949 | 7/1990 | Borch et al. | 424/10 |
| 4,956,345 | 9/1990 | Miyasaka et al. | 514/46 |
| 5,070,877 | 12/1991 | Mohiuddin et al. | 128/653.4 |
| 5,096,906 | 3/1992 | Mandell et al. | 514/263 |
| 5,124,455 | 6/1992 | Lombardo et al. | 546/181 |
| 5,140,015 | 8/1992 | Olsson et al. | 514/46 |
| 5,272,153 | 12/1993 | Mandell et al. | 514/263 |
| 5,278,150 | 1/1994 | Olsson et al. | 514/46 |
| 5,565,462 | 10/1996 | Eitan et al. | 514/262 |
| 5,593,975 | 1/1997 | Cristalli | 514/46 |
| 5,665,754 | 9/1997 | Feldman et al. | 514/397 |
| 5,776,940 | 7/1998 | Daluge et al. | 514/263 |
| 5,854,081 | 12/1998 | Linden et al. | 436/501 |
| 5,877,180 | 3/1999 | Linden et al. | 514/266 |
| 5,932,558 | 8/1999 | Cronstein et al. | 514/46 |

FOREIGN PATENT DOCUMENTS

| | | |
|---|---|---|
| 0203721 | 12/1986 | European Pat. Off. . |
| 0700908 | 3/1996 | European Pat. Off. . |
| 90/00056 | 1/1990 | WIPO . |
| 9511681 | 5/1995 | WIPO . |
| 9604280 | 2/1996 | WIPO . |
| 9847509 | 10/1998 | WIPO . |

OTHER PUBLICATIONS

Andersson, P., et al., "Anti–anaphylactic and anti–inflammatory effects of xanthines in the lung", *Curr. Clin. Pract. Ser.*, , 187–192, (1985).

Berkich, D.A., et al., "Evidence of Regulated Coupling of A1 Adenosine Rececptors by Phosphorylation in Zucker Rats.", *American Physiological Society*, 268(4 Pt 1), E693–E704, (Apr., 1995).

Bhattacharya, S., et al., "Effects of Long–term Treatment With the Allosteric Enhancer, PD81, 723, on Chinese Hamster Ovary Cells Expressing Recombinant Human $A_1$ Adenosine Receptors", *Molecular Pharmacology*, 50(1), 104–111, (Jul., 1996).

Bhattacharya, S., et al., "The Allosteric Enhancer, PD 81, 723, Stabilizes Human $A_1$ Adenosine Receptor Coupling to G Proteins", *Biochimica Biophysica Acta*, 1265(1), 15–21, (Feb. 1995).

Bridges, A.J., et al., "$N^6$–[2–(3, 5–Dimethoxyphenyl)–2–(2–Methylphenyl)–Ethyl]Adenosine and Its Uronamide Derivatives. Novel Adenosine Agonists With Both High Affinity and High Selectivity for the Adenosine $A_2$ Receptor", *Journal of Medicinal Chemistry*, 31(7), 1282–1285, (1988).

Buster, B., et al., "The Effect of Adenosine Receptor Agonists on Neutrophil Pleocytosis and Blood–Brain Barrier Pathophysiology in Experimental Bacterial Meningitis", *Abstract of the Interscience Conference on Antimicrobial Agents and Chemotherapy*, 37, 39, (1997).

Cembrzynska, N.M., et al., "Elevated Release of Tumor Necrosis Factor–alpha and Interferon–gamma by Bronchoalveolar Leukocytes From Patients With Bronchial Asthma.", *American Review of Respiratory Disease*, 147(2), 291–295, (1993).

Cothran, D.L., et al., "Ontogeny of Rat Myocardial $A_1$ Adenosine Receptors", *Biol Neonate*, 68(2), 111–118, (1995).

Cristalli, G., et al., "Alkynyl Derivatives of Adenosine an Adenosine–5'–N–ethyluronamide as Selective Agonists at $A_2$ Adenosine Receptors", *Journal of Medicinal Chemistry*, 35(13), 2363–2368, (1992).

Cronstein, B.N., et al., "Adenosine Modulates the Generation of Superoxide Anion by Stimulated Human Neutrophils Via Interaction With a Specific Cell Surface Receptor", *Annals New York Academy of Science*, 451, 291–314, (1985).

Cronstein, B.N., et al., "Adenosine; A Physiologic Modulator Of Superoxide Anion Generated By Human Neutrophils. Adenosine Acts Via An $A_2$ Receptor On Human Neutrophils", *Journal of Immunology*, 135(2), 1366–1371, (1985).

Cronstein, B.N., et al., "Engagement of Adenosine Receptors Inhibits Hydrogen Peroxide ($H_2O_2$) Release by Activated Human Neutrophils", *Clinical Immunology and Immunopathology*, 42(1), 76–85 (1987).

Cronstein, B.N., et al., "Methotrexate Inhibits Leukocyte Influx Into Inflammatory Sites Via The Adenosine ($A_2$) Receptor", *Clinical Research*, 41(2), 244A, (1993).

Cronstein, B.N., et al., "The Adenosine/Neutrophil Paradox Resolved: Human Neutrophils Possess Both $A_1$ and $A_2$ Receptors That Promote Chemotaxis and Inhibits $O_2$ Generation, Respectively", *Journal of Clinical Investigation*, 85(4), 1150–1157, (1990).

Cronstein, N., et al., "Occupancy of Adenosine Receptors Raises Cyclic AMP Alone And In Synergy With Occupancy Of Chemoattractant Receptors And Inhibits Membrane Depolarization", *Biochemical Journal*, 252(3), 709–715, (1988).

(List continued on next page.)

*Primary Examiner*—William R. A. Jarvis
*Attorney, Agent, or Firm*—Schwegman, Lundberg, Woessner & Kluth, P.A.

[57] ABSTRACT

The invention concerns the use of 8-phenylxanthines, 8-cyloalkylxanthines or 8- substituted xanthine derivatives to specifically modulate the physiologic role of the A2B adenosine receptor.

12 Claims, 6 Drawing Sheets

OTHER PUBLICATIONS

De La Harpe, J., et al., "Adenosine Regulates the Respiratory Burst Of Cytokine –Triggered Human Neutrophils Adherent To Biological Surfaces", *Journal Of Immunology*, 143(2), 596–602, (1989).

Dinerallo, C.A., "Interleukin–1 And Tumor Necrosis Factor: Effector Cytokines In Autoimmune Diseases", *Seminars in Immunology*, 4, 133–145, (1992).

Doyle, M.P., et al., "Nucleoside–induced Arteriolar Constriction: a Mast Cell–dependent Response.", *American Journal of Physiology*, H2042–H2050, (May, 1994).

Feoktistov, I., et al., "Adenosine $A_{2b}$ Receptors", *The American Society for Pharmacological and Experimental Therapeutics*, 49(4), 381–402 (1997).

Feoktistov, I., et al., "Role of Adenosine in Asthma", *Drug Development Research*, 39, 333–336, (1996).

Ferrante, A., et al., "Optimal Conditions for Simultaneous Purification of Mononuclear and Polymorphonuclear Leucocytes From Human Blood by the Hypaque–Ficoll Method", *Journal of Immunological Methods*, 36(2), 109, (1980).

Figler, R.A., et al., "Reconstitution of Bovine $A_1$ Adenosine Receptors and G Proteins in Phospholipid Vesicles: βY–Subunit Composition Influences Guanine Nucleotide Exchange and Agonist Binding", *Biochemistry*, 36(51), 16288–16299, (1997).

Figler, R.A., et al., "Reconstitution of Recombinant Bovine $A_1$ Adenosine Receptors in Sf9 Cell Membranes with Recombinant G Proteins of Defined Composition.", *Molecular Pharmcology*, 50(6), 1587–1595, (Dec. 1996).

Firestein, G.S., et al., "Adenosine Regulating Agents: A Novel Approach to Inflammation and Inflammatory Arthritis", *Clinical Research*, 41(2), 170A, (1993).

Francis, J.E., et al., "Highly Selective Adenosine $A_2$ Receptor Agonists in a Series of N–Alkylated 2–Aminodenosines", *Journal of Medicinal Chemistry*, 34(8), 2570–2579, (1991).

Gao, Z., et al., "$A_{2B}$ Adenosine and $P2Y_2$ Receptors Stimulate Mitogen–activated Protein Kinase in Human Embryonic Kidney–293 Cells. Cross–talk Between Cyclic AMP and Protein Kinase c Pathways", *Journal of Biological Chemistry*, 274(9), 5972–5980, (Feb. 1999).

Gao, Z., et al., "Purification of $A_1$ Adenosine Receptor–G–protein Complexes: Effects of Receptor Down–regulation and Phosphorylation on Coupling", *Biochemical Journal*, 338(Pt3), 729–736, (Mar., 1999).

Gilchrist, A., et al., "Antagonists of the Receptor–G Protein Interface Block $G_1$–coupled Signal Transduction", *Journal of Biological Chemistry*, 273(24), 14912–14919, (Jun., 1998).

Glover, D.K., et al., "Pharmacological Stress Thallium Scintigraphy With 2–Cyclohexlmethylidenehydrazinoadenosine (WRC–0470) A Novel, Short–Acting Adenosine A2A Receptor Agonist.", *Circulation*, 94, 1726–1732, (1996).

Griswold, D.E., et al., "Effects of Selective Phosphodieasterase Type IV Inhibitor, Rolipram, on Fluid and Cellular Phases of Inflammatory Response", *Chemical Abstract*, 119, Abstract No. 173828e, (1993).

Hanlon, W.A., et al., "rTNFα Facilitate Human Polymorphonuclear Leukocyte Adherence to Fibrinogen Matrices With Mobilization of Specific and Tertiary But Not Azurophilic Granule Markers", *Journal of Leukocyte Biology*, 50(1), 43–48, (1991).

Holmes, et al., "Restenosis After Percutaneous Transluminal Coronary Angioplasty (PTCA): A Report From the PTCA Registry of the National Heart, Lung, and Blood Institute", *American Journal of Cardiology*, 53, 77C–81C, (1984).

Hussain, T., et al., "$^{125}$1–APE Binding to Adenosine Receptors in Coronary Artery: Photoaffinity Labeling With $^{125}$1–azidoAPE", *Journal of Pharmacology and Experimental Therapeutics*, 276(1), 284–288, (Jan. 1996).

Hutchison, A.J., et al., "2–(Arylalkylamino)Adenosine–5'–Uronamides: A New Class of Highly Selective Adenosine $A_2$ Receptor Ligands", *Journal of Medicinal Chemistry*, 33(7), 1919–1924, (1990).

Hutchison, A.J., et al., "CGS 21680C, an $A_2$ Selective Adenosine Receptor Agonist With Preferential Hypotensive Activity", *Journal of Pharmacology and Experimental Therapeutics*, 251(1), 47–55, (1989).

Iannone, M.A., et al., "Effects of Adenosine on Human Neutrophil Function and Cyclic AMP Content", *Topics and Perspectives in Adenosine Research, eds. E. Gerlach et al., Springer–Verlag, Berlin*, Proceedings of the 3rd International Symposium on Adenosine, Munich, Jun. 1986, 286–298, (1986).

Imagawa, D.K., et al., "The Role of Tumor Necrosis Factor in Allograft Rejection", *Transplantation*, 51, 57–62, (Jan. 1991).

Jarvis, M.F., et al., "[$^3$H]CGS 21680, A Selective $A_2$ Adenosine Receptor Agonist Directly Labels A2 Receptors in Rat Brain.", *Journal of Pharmacology and Experimental Therapeutics*, 251(3), 888–893, (Aug. 1989).

Kaminuma, et al., "Effect of T–440, a Novel Type IV Phosphodiesterase Inhibitor, on Allergen–Induced Immediate and Late Asthmatic Reaction and Leukocyte Infiltration into the Airways of Guinea Pigs", *International Archives of Allergy & Immunology*, 112(4), 406–411, (1997).

Kennedy, A.P., et al., "Covalent Modification of Transmembrane Span III of the $A_1$ Adenosine Receptor With an antagonist Photoaffinity Probe.", *Molecular Pharmacology*, 50, 789–798, (Oct. 1996).

Kollias–Baker, C., et al., "Allosteric Enhancer PD 81,723 Acts by Novel Mechanism to Potentiate Cardiac Actions of Adenosine", *Circulation Research*, 75(6), 961–971, (Dec. 1994).

Koshiba, M., et al., "Patterns of $A_{2A}$ Extracellular Adenosine Receptor Expression in Different Functional Subsets of Human Peripheral T Cells. Flow Cytometry Studies With Anti–$A_{2A}$ Receptors Monoclonal Antibodies.", *Molecular Pharmacology*, 55(3), 614–624, (Mar., 1999).

Legrand–Poels, S., et al., "Activation of Human Immunodeficiency Virus Type 1 by Oxidative Stress", *AIDS Research and Human Retroviruses*, 6(12), 1389–1397, (1990).

Lette, J., et al., "Safety of Dipyridamole Testing in 73,806 Patients: The Multicenter Dipyridamole Safety Study", *Journal of Nuclear Cardiology*, 2(1), 3–17, (1995).

Linden, J., "Allosteric Enhancement of Adenosine Receptors", *Purinergic Approaches in Experimental Therapeutics, Editors: Jacobson, Kenneth A. (Ed) & Jarvis, Michael F (Ed.)*, 85–87, (1997).

Linden, J., "Cloned Adenosine $A_3$ Receptors: Pharmacological Properties, Species Differences and Receptor Functions.", *Trends in Pharmacological Sciences*, 15(8), 298–306, (Aug. 1994).

Linden, J., "Recombinant Techniques as Applied to the Study of A₁ Adenosine Receptors", *Adenosine Adenine Nucleotides Molecular Biology Integrative Physiology, Editors: Belardinelli, Luiz (Ed) & Pelleq, Amir (Ed.)*, 15–19.

Linden, J., et al., "The Structure and Function of $A_1$ and $A_{2B}$ Adenosine Receptors", *Life Science*, 62(17–18), 1519–1524, (1998).

Luthin, D.R., et al., "Adenosine Receptors", *Biomembranes*, 2B, 321–347, (1996).

Luthin, D.R., et al., "Characterization of Two Affinity States of Adenosine $A_{2a}$ Receptors With a New Radioligand, 2–[2–(4–amino–3–[$^{125}$I]iodophenyl) Ethylamino]Adenosine.", *Molecular Pharmacology*, 47(2), 307–313, (Feb. 1995).

Luthin, D.R., et al., "Comparison of $A_4$ and $A_{2a}$ Binding Sites in Striatum and COS Cells Transfected With Adenosine $A_{2a}$ Receptors.", *Journal of Pharmacology and Experimental Therapeutics*, 272, 511–518, (Feb. 1995).

Luthin, D.R., et al., "Photoaffinity Labeling With 2(–) [2–(4–azido–3(–)[$^{125}$I]–iodophenyl)ethylamino]Adenosine and Autoradiography With 2(–)[2–(4–amino–3(–)[$^{125}$I]iodophenyl)ethylamino]Adenosine of $A_{2a}$ Adenosine Receptor in Rat Brain.", *Journal of Neurochemistry*, 65(5), 2072–2079, (Nov. 1995).

Mannel, D.N., et al., "Tumor Necrosis Factor: A Cytokine Involved in Toxic Effects of Endotoxin", *Reviews of Infectious Diseases*, 9, S602–S606, (1987).

Martin, P.L., et al., "Characterization of 8–(N–methylisopropyl)amino–$N^6$–(5'–andohydroxy–endonorbornyl)–9–methyladenine (WRC–0571), a Highly Potent and Selective, Non–xanthine Antagonist of $A_1$ Adenosine Receptors.", *Journal of Pharmacology and Experimental Therapeutics*, 276(2), 490–499, (Feb. 1996).

Martin, P.L., et al., "Pharmacology of 2–cyclohexylmethylidenehydrazinoadenosine (WRC–0470), a Novel, Short–acting Adenosine $A_{2A}$ Receptor Agonist That Produces Selective Coronary Vasodilation.", *Drug Development Research*, 40(4), 313–324, (1997).

Matherne, G.P., et al., "Transgenic A1 Adenosine Receptor Overexpression Increases Myocardial Resistance to Ischemia", *Proceedings of the National Academy of Science, USA*, 94, 6541–6546, (Jun. 1997).

Matsuyama, T., et al., "Cytokines and HIV Infection: is AIDS a Tumor Necrosis Factor Disease?", *AIDS*, 5(12), 1405–1417, (1991).

McGarrity, S.T., et al., "Inhibition of Neutrophil Superoxide Anion Generation by Platelet Products: Role of Adenine Nucleotide", *Journal of Leukocyte Biology*, 44(5), 411–421, (1988).

McGarrity, S.T., et al., "Regulation of Human Neutrophil Function by Adenine Nucleotides", *Journal of Immunology*, 142(6), 1986–1994, (1989).

McLaughlin, D.P., et al., "Hemodynamic and Metabolic Correlates of Dipyridamole–induced Myocardial Thallium–201 Perfusion Abnormalities in Multivessel Coronary Artery Disease.", *American Journal of Cardiology*, 73(16), 1159–1164, (Jun., 1994).

Merritt, H.R., et al., "Abnormal Q Waves are Common Early in AMI and Do Not Predict Decreased Myocardial Salvage With Thrombolytic Therapy", *Journal of American College of Cardiology*, 895–897, (Feb. 1994).

Mizumura, T., et al., "PD 81,723, an Allosteric Enhancer of the $A_1$ Adenosine Receptor, Lowers the Threshold for Ischemic Preconditioning in Dogs.", *Circulation Research*, 79(3), 415–423, (Sep. 1996).

Molnar–Kimber, K.L., et al., "Modulation of TNFα and IL–1β From Endotoxin–Stimulated Monocytes by Selective PDE Isozyme Inhibitors", *Agents & Actions*, 39, C77–C79, (1993).

Nabel, E.G., et al., "Site–Specific Gene Expression in Vivo by Direct Gene Transfer into the Arterial Wall", *Science*, 249, 1285–1288, (1990).

Newman, K.D., et al., "Adenovirus–mediated Gene Transfer into Normal Rabbit Arteries Results in Prolonged Vascular Cell Activation, Inflammation and Neointimal Hyperplasia", *Journal of Clinical Investigation*, 96(6), 2955–2965, (1995).

Nielson, C.P., et al., "Effects of Adenosine on Polymorphonuclear Leucocyte Function, Cyclic 3': 5'–adenosine Monophosphate, and Intracellular Calcium", *British Journal of Pharmacology*, 97(3), 882–888, (1989).

Niiya, K., et al., "2–(N'–Alkylidenehydrazino)Adenosine: Potent and Selective Coronary Vasodilators", *Journal of Medicinal Chemistry*, 35(24), 4557–4561, (1992).

Nolte, "Reduction of Postischemic Leukocyte–Endothelium Interaction by Adenosine Via $A_2$ Receptor" *Biological Abstract*, 94(11), Abstract No. 116779, (1992).

O'Regan, M.H., et al., "Adenosine Receptor Agonists Inhibit the Release of Y–Aminobutyric Acid (GABA) From the Ischemic Rat Cerebral Cortex", *Chemical Abstracts*, 117, Abstract No. 104867p, 170, (1992).

Olsson, R.A., et al., "$N^6$ Substituted N–Alkyladenosine–5'–Uronamides: Bifunctional Ligands Having Recognition Groups for A1 and A2 Adenosine Receptors", *Journal of Medicinal Chemistry*, 29(9), 1683–1689, (1986).

Peet, N.P., et al., "Conformationally Restrained, Chiral (Phenylisopropyl)Amino–Substituted Pyrazolo[3,4–d]Pyrimidines and Purines With Selectivity for Adenosine $A_1$ and $A_2$ Receptors", *Journal of Medicinal Chemistry*, 35(17), 3263–3269, (1992).

Pfister, J.R., et al., "Synthesis and Biological Evaluation of the Enantiomers of the Potent and Selective $A_1$– adenosine Antagonist 1,3–dipropyl–8–[2–(5,6–epoxynorbonyl)]–xanthine", *Journal of Medicinal Chemistry*, 40(12), 1773–1778, (Jun., 1997).

Ranhosky, A., et al., "The Safety of Intravenous Dipyridamole Thallium Myocardial Perfusion Imaging", *Circulation*, 81(4), 1205–1209, (Apr., 1990).

Roberts, P.A., et al., "Inhibition by Adenosine of Reactive Oxygen Metabolite Production by Human Polymorphonuclear Leucocytes", *Biochemical Journal*, 227(2), 669–674, (1985).

Robeva, A.S., et al., "Double Tagging Recombinant $A_1$– and $A_{2a}$–Adenosine Receptors With Hexahistidine and the FLAG Epitope. Development of an Efficient Generic Protein Purification Procedure.", *Biochemical Pharmacology*, 51(4), 545–555, (Feb. 1996).

Rosin, D.L., et al., "Immunohistochemical Localization of Adenosine $A_{2A}$ Receptors in the Rat Central Nervous System", *Journal of Comparative. Neurology*, 402(2), 163–186, (Nov. 1998).

Rothe, G.A., et al., "Flow Cytometric Measurement of the Respiratory Burst Activity of Phagocyte Using Dihydrorhodamine 123", *Journal of Immunological Methods*, 138(1), 133–135, (1991).

Sawmiller, D.R., et al., "Effects of Xanthine Amine Congener on Hypoxic Resistance and Venous and Epicardial Adenosine Concentrations.", *Cardiovascular Research*, 28(5), 604–609, (May, 1994).

Schlack, et al., "Adenosine $A_2$–Receptor Activation at Reperfusion reduces Infarct Size and Improves Myocardial Wall Function in Dog Heart", *Biological Abstract*, 96(6), Abstract No. 67801, (1993).

Schrier, D.J., et al., "Effects of Adenosine Agonists on Human Neutrophil Function", *Journal of Immunology*, 137(10), 3284–3289, (1986).

Seekamp, A., et al., "Ischemia—Reperfusion Injury", *Agents and Actions Supplements*, 41, 137–152, (1993).

Sharief, M.K., et al., "Elevated Serum Levels of Tumor Necrosis Factor–α in Guillain–Barre Syndrome", *Annals of Neurology*, 33, 591–596, (Jun. 1993).

Shephard, R.K., et al., "Adenosine–induced Vasoconstriction in Vivo. Role of the Mast Cell and $A_3$ Adenosine Receptor.", *Circulation Research*, 78(4), 627–634, (Apr., 1996).

Sipka, S., et al., "Adenosine Induced Delay of Expression of AIDS Virus, HIV, in H9T Cells", *Acta. Biochimica et Biophysica Hungarica*, 23(1), 75–82, (1988).

Siragy, H.M., et al., "Sodium Intake Markedly Alters Renal Interstitial Fluid Adenosine", *Hypertension*, 27(3 Pt 1), 404–407, (Mar., 1996).

Smits, P., et al., "Cardiovascular effects of two xanthines and the relation to adenosine antagonism", *Clinical Pharmacology and Therapeutics*, 45(6), 593–599, (1989).

Sullivan, G.W., et al., "Adenosine (ADO) Modulates Endotoxin and TNF–Induced PMN Activation", *Clinical Research*, 41(2), 172A, (1993).

Sullivan, G.W., et al., "Role of $A_{2A}$ Adenosine Receptors in Inflammation", *Drug Development Research*, 45(3/4), 103–112, (1998).

Sullivan, G.W., et al., "The Specific Type IV Phosphodiesterase Inhibitor Rolipram Combined with Adenosine Reduces Tumor Necrosis Factor–α–Primed Neutrophil Oxidative Activity", *International Journal of Immunonopharmacology*, 17(10), 793–803, (1995).

Sullivan, G.W., et al., "Two Methylxanthines, Pentoxifylline (PTX) and Caffeine (CAF) Have Divergent Effects on Tumor Necrosis Factor (TNF)–Primed Human Neutrophil (PMN) Activation", *Clinical Research*, 41(2), 172A, (1993).

Topol, E.J., et al., "Randomised Trial of Coronary Intervention With Antibody Against Platelet IIb/IIIa integrin for Reduction of Clinical Restenosis: Results at Six Months", *The Lencet*, 343(8902), 881–886, (1994).

Tracey, K.J., et al., "Cachectin/Tumor Necrosis Factor Induces Cachexia, Anemia, and Inflammation", *Journal of Experimental Medicine*, 167, 1211–1227, (Mar. 1988).

Tucker, A.L., et al., "$A_1$ Adenosine Receptors. Two Amino Acids are Responsible for Species Differences in Ligand Recognition", *Journal of Biological Chemistry*, 269(45), 27900–27906, (Nov. 1994).

Ueeda, M., et al., "2– Alkoxyadenosines: Potent and Selective Agonists at the Coronary Artery $A_2$ Adenosine Receptor", *Journal of Medicinal Chemistry*, 34(4), 1334–1339, (1991).

Underwood, D.C., et al., "Inhibition of Antigen–Induced Bronchoconstriction and Eosinophil Infiltration in the Guinea by the Cyclic AMP–Specific Phosphodiesterase Inhibitor, Rolipram", *Chemical Abstracts*, 119(16), Abstract No. 173975a, 67, (1993).

Van Calker, D., et al., "Carbamazepine Distinguishes Between Adenosine Receoters That Mediate Different Second Messenger Responses", *European Journal of Pharmacology*, 206(4), 285–290, (1991).

Walker, B.A., et al., "Adenosine $A_{2a}$ Receptor Activation Delays Apoptosis in Human Neutrophils", *The American Association of Immunologists*, 2926–2931, (1997).

Yoneyama, F., et al., "Vasodepressor Mechanisms of 2–(1–octynyl) –Adenosine (YT–146), a Selective Adenosine $A_2$ Receptor Agonist, Involve the Opening of Glibenclamide–sensitive $K^+$ Channels", *European Journal of Pharmacology*, 213(1), 199–204, (1992).

"Molecular Characterization of Recombinant Human Adenosine Receptors", *Drug Development Research*, vol. 39, 243–252, (1996).

Auchampach, J.A., et al., "Canine Mast Cell Adenosine Receptors", *Mol. Pharmacol*, vol. 52, 846–860, (1997).

Barnes, P.J., et al., "Theophylline in the Management of asthma: Time for Reappraisal?.", *European Respiratory Journal*, vol. 7, 579–591, (1994).

Bjorck, T., et al., "Isolated Bronchi from Asthmatics are Hyper Responsive to Adenosine", *Am. Rev. Respir. Dis.*, vol. 145, 1087–1091, (1992).

Bruns, R.F., et al., *Mol. Pharmacol.*, vol. 29, 331–346, (1986).

Chapman, K.R., et al., "Long–term Xanthine Therapy of Asthma. Enprofylline and Theophylline Compared", *International Enprofylline Study Group, Chest*, vol. 106, 1407–1413, (1994).

Feoktistov, I., et al., "Adenosine A2B Receptors Evoke Interleukin–8 Secretion in Human Mast Cells—An Enprofylline–sensitive Mechanism with Implications for Asthma", *J. Clin. Invest.*, vol. 96, 1979–1986, (1995).

Jin, X., et al., "Inosine Binds to A3 Adenosine Receptors and Stimulates Mast Cell Degranulation", *J. Clin. Invest.*, vol. 100, 2849–2857, (1997).

Lunell, et al., "Effects of Enprofylline, a Xanthine Lacking Adenosine Receptor Antagonism, in Pateitns with Chronic Obstructive Ling Disease", *European Journal of Clinical Pharmacology*, vol. 22, 395–402, (1982).

Ramkumar, V., et al., "The A3 Adenosine Receptor is the Unique Adenosine Receptor which Facilitates Release of Allergic Mediators in Mast Cells", *J. Biol. Chem.*, vol. 268, 16887–16890, (1993).

Ukena, et al., *FEBS Lett.*, vol. 209, 122–128, (1986).

8-PHENYL- OR 8-CYCLOALKYL XANTHINE ANTAGONISTS OF A2B HUMAN ADENOSINE RECEPTORS

BACKGROUND OF THE INVENTION

1. Field of the Invention

The present invention relates to methods for the treatment or prevention of disease states induced by activation of the A2B receptor and mast cell activation.

2. Description of the Related Art

A key early event in allergic responses is the activation of mast cells by allergens. For example, in asthma, exposure to an allergen such as ragweed, triggers the release of allergic mediators such as histamine, leukotrienes, etc. from mast cells. The action of allergens to trigger mast cell degranulation is enhanced by adenosine in asthmatics, but not in non-asthmatics (Bjorck T, Gustafsson L E, Dahlen S E: Isolated bronchi from asthmatics are hyper responsive to adenosine, which apparently acts indirectly by liberation of leukotrienes and histamine. Am.Rev.Respir.Dis. 1992;145:1087–1091). Theophylline is a xanthine that is known to block adenosine receptors and is effective therapeutically to treat asthma (Barnes P J, Pauwels R A: Theophylline in the management of asthma: time for reappraisal?. European.Respiratory.Journal. 1994;7:579–591). For this reason, theophylline is thought to ameliorate the symptoms of asthma, at least in part by blocking adenosine receptors. However, enprofylline, another xanthine that also is used to treat asthma in Europe, was found not to block adenosine receptors in the therapeutic concentration range of 20–50 uM (Chapman K R, Ljungholn K, Kallen A: Long-term xanthine therapy of asthma. Enprofylline and theophylline compared. International Enprofylline Study Group. Chest 1994; 106:1407–1413). Hence it was concluded that enprofylline does not work by blocking adenosine receptors. However, this conclusion was based on an examination of enprofylline binding only to two of the four known adenosine receptor subtypes, A1 and A2A receptors.

Applicant and others have recently discovered that the A3 adenosine receptor on mast cells are responsible for adenosine-stimulated release of allergic mediators in rodent species (Jin X, Shepherd R K, Duling B R, Linden J: Inosine binds to A3 adenosine receptors and stimulates mast cell degranulation. J.Clin.Invest. 1997;100:2849–2857; Ramkumar V, Stiles G L, Beaven M A, Ali H: The $A_3$ adenosine receptor is the unique adenosine receptor which facilitates release of allergic mediators in mast cells. J.Biol.Chem. 1993;268:16887–16890). These findings are misleading in that applicant has found that the A3 receptor is not involved in the release of allergic mediators from other species, including human and dog. Rather, applicant discovered that in canine and human mast cells the A2B and not the A3 adenosine receptor is responsible for adenosine-facilitated mast cell degranulation (Auchampach J A, Jin J, Wan T C, Caughey G H, Linden J: Canine mast cell adenosine receptors: cloning and expression of the A3 receptors and evidence that degranulation is mediated by the A2B receptor. Mol.Pharmacol. 1997;52:846–860). FIG. 1 of the instant application shows that NECA (a nonselective agonist that activates A2B and A3 receptors) causes intracellular $Ca^{2+}$ and cyclic AMP accumulation in the human mast cell line, HMC-1. IB-MECA, a potent and selective agonist of the A3 receptor is poorly effective. These data suggest that the A2B receptor mediates these responses in HMC-1 human mast cells. Another published report also suggests that activation of A2B receptors is responsible for triggering interleukin-8 release from human HMC-1 mast cells (Feoktistov I, Biaggioni I: Adenosine $A_{2B}$ receptors evoke interleukin-8 secretion in human mast cells—An enprofylline-sensitive mechanism with implications for asthma. J. Clin. Invest. 1995;96: 1979–1986).

8-Phenylxanthines, methods of their synthesis and their use in human and veterinary therapy for conditions associated with the cell surface effects of adenosine have been described (EP 0 203 721, published Dec. 13, 1986). However, this publication is silent as to whether adenosine receptors mediate this response and if so, which adenosine receptor subtype. Also, the subtype specificity of disclosed compounds is not described. In WO 90/00056, a group of 1,3-unsymmetrical straight chain alkyl-substituted 8-phenylxanthines were described as being potent bronchodilators. This disclosure is likewise silent as to the role of adenosine and the subtype specificity of disclosed compounds.

Methods of treating conditions related to the physiological action of adenosine have, to date, proven inferior due to the presence of multiple subtypes present in the animal tissue utilized (R. F. Bruns et al., (1986) Mol. Pharm. 29:331–346) and the differences between species in the affinity for adenosine analogs and the physiological effects of adenosine (Ukera et al., (1986) FEBS Lett, 209:122–128).

SUMMARY OF THE INVENTION

The present invention concerns the use of compounds identified as specific modulators of adenosine's physiological actions. The pharmacology of these compounds is characterized through the use of cloned human adenosine receptors of the A1, A2A, A2B and A3 class and their subtypes. Applicant has found that compounds identified as antagonists of the A2B adenosine receptor subtype are useful in preventing mast cell degranulation and are therefore useful in the treatment or prevention of disease states induced by activation of the A2B receptor and mast cell activation. These disease states include but are not limited to asthma, myocardial reperfusion injury, allergic reactions including but not limited to rhinitis, poison ivy induced responses, urticaria, scleroderm arthritis, other autoimmune diseases and inflammatory bowel diseases. The present invention is based on the finding that antagonists of the A2B adenosine receptor subtype have anti-inflammatory action.

Through the use of homogenous, recombinant adenosine receptors, the identification and evaluation of compounds which have selectivity for a single receptor subtype have now been accomplished. Moreover, because of the variable effects of adenosine documented in other species, the utilization of human adenosine receptor subtypes is advantageous for the development of human therapeutic adenosine receptor agonists, antagonists or enhancers. In previous research conducted by the Applicant, compounds which unexpectedly exhibit selective binding affinity for the human A2B adenosine receptor were identified, along with methods for using such compounds to overcome the disadvantages of using compounds of uncharacterized specificity. The compounds specifically block activities mediated through the activation of the A2B receptor subtype without substantially blocking the activities of other adenosine receptor subtypes. In particular, Applicant found that the use of such compounds, identified through the use of recombinant human adenosine receptors A1, A2A, A2B and A3, and functional assays, can specifically modulate the physiologic role of adenosine activation of various receptors.

Applicant has developed for the first time a radioligand binding assay for the A2B adenosine receptor (Linden, J. et al. U.S. patent application Ser. No. 08/670,175, filed Jun. 20, 1996, the entire disclosure of which is herein incorporated by reference). Using this assays system, applicant has discovered that enprofylline, in the therapeutic concentration range of 20–50 µM used to treat asthma, blocks recombinant human A2B adenosine receptors, but is a much weaker antagonist of other adenosine receptor subtypes (FIG. 2 and Table 1).

The release of enzymes, bioactive amines and arachidonic acid metabolites following mast cell activation causes vasoconstriction, edema, leukocyte accumulation, and ultimately, tissue damage. Mast cell degranulation is a component of mycardian reperfusion injury, hypersensitivity reactions (asthma, allergic rhinitis, and urticaria), ischemic bowel disease, autoimmune inflammation, and atopic dermatitis. Highly specific A2B adenosine receptor antagonists can be used to treat or prevent these diseases and pathologic effects that result from mast cell degranulation.

Mast cell degranulation is clearly involved in the pathophysiology of allergies such as asthma. Autoimmune diseases are also characterized by immune reactions which attack targets, including self-proteins in the body such as collagen, mistaking them for invading antigens. The resulting damage, caused at least in part by mast cell degranulation, is amenable to treatment by the method of this invention which comprises administration of selective A2B adenosine receptor antagonists effective to inhibit mast cell degranulation. Among these types of diseases, all of the following, but not limited to these, are amenable to treatment by the administration of selective A2B adenosine receptor antagonists: Addison's disease (adrenal), autoimmune hemolytic anemia (red cells), Crohn's disease (gut), Goodpasture's syndrome (idney and lungs), Grave's disease (thyroid), Hashimoto's thyroiditis (thyroid), idiopathic thrombocytopinic purpura (platelets), Insulin-dependent diabetes militus (pancreatic beta cells), multiple sclerosis (brain and spinal cord), myasthenia gravis (nerve/muscle synapses), *Pemphigus vulgaris* (skin), pernicious anemia (gastric parietal cells), poststreptococcal glomerulonephritis (kidney), psoriasis (skin), rheumatoid arthritis (connective tissue), sclerodenna (heart, lung, gut, kidney), Sjogren's syndrome (liver, kidney, brain, thyroid, salivary gland), spontaneous, infertility (sperm), systemic lupus erythematosus (DNA, platelets, other tissues).

Disease states associated with A2B adenosine receptor activation and mast cell degranulation include, but are not limited to asthma, myocardial reperfusion injury, allergic reactions including but not limited to rhinitis, asthma, poison ivy induced responses, urticaria, scleroderma, arthritis, and inflammatory bowel diseases.

The present invention is directed to the discovery that antagonists of A2B receptors are anti-inflammatory in man. A3 adenosine receptors also have an anti-inflammatory action, but are most important in rodent species. It has been found that enprofylline, a compound already used to treat asthma, blocks A2B adenosine receptors and that human HMC-1 mast cells have A2B receptors and that 8-phenylxanthines that block human A2B adenosine receptors-are-useful in the treatment or prevention of disease states induced by activation of the A2B receptor and mast cell activation. Also, applicant has discovered that BW-A493 is a potent and selective antagonist of human A2B adenosine receptors (Table 1).

A further aspect of the invention is the treatment of prevention of asthma, bronchoconstriction, allergic potentiation, inflammation or reperfusion injury in a human by administering to the human an amount of an adenosine A2B receptor specific inhibitor comprising an 8-phenylxanthine or 8-phenylxanthine derivative effective to antagonize activation of the adenosine receptor of the A2B subtype by adenosine.

The invention also relates to a method for treating a human suffering from an autoimmune disease selected from the group consisting of Addison's disease (adrenal), autoimmune hemolytic anemia (red cells), Crohn's disease (gut), Goodpasture's syndrome (kidney and lungs), Grave's disease (thyroid), Hashimoto's thyroiditis (thyroid), idiopathic thrombocytopinic purpura (platelets), insulin-dependent diabetes militus (pancreatic beta cells), multiple sclerosis (brain and spinal cord), myasthenia gravis (nerve/muscle synapses), *Pemphigus vulgaris* (skin), pernicious anemia (gastric parietal cells), post-streptococcal glomerulonephritis (kidney), psoriasis (skin), rheumatoid arthritis' (connective tissue), scleroderma (heart, lung, gut, kidney), Sjogren's syndrome (liver, kidney, brain, thyroid, salivary gland), spontaneous infertility (sperm), and systemic lupus erythematosus (DNA, platelets, other tissues), which comprises administering to the human an effective amount of a selective A2B adenosine receptor antagonist comprising a xanthine or a xanthine derivative having a meta-substituted acidic aryl at the 8 position to inhibit mast cell degranulation.

DETAILED DESCRIPTION OF THE INVENTION

Figure 1A:
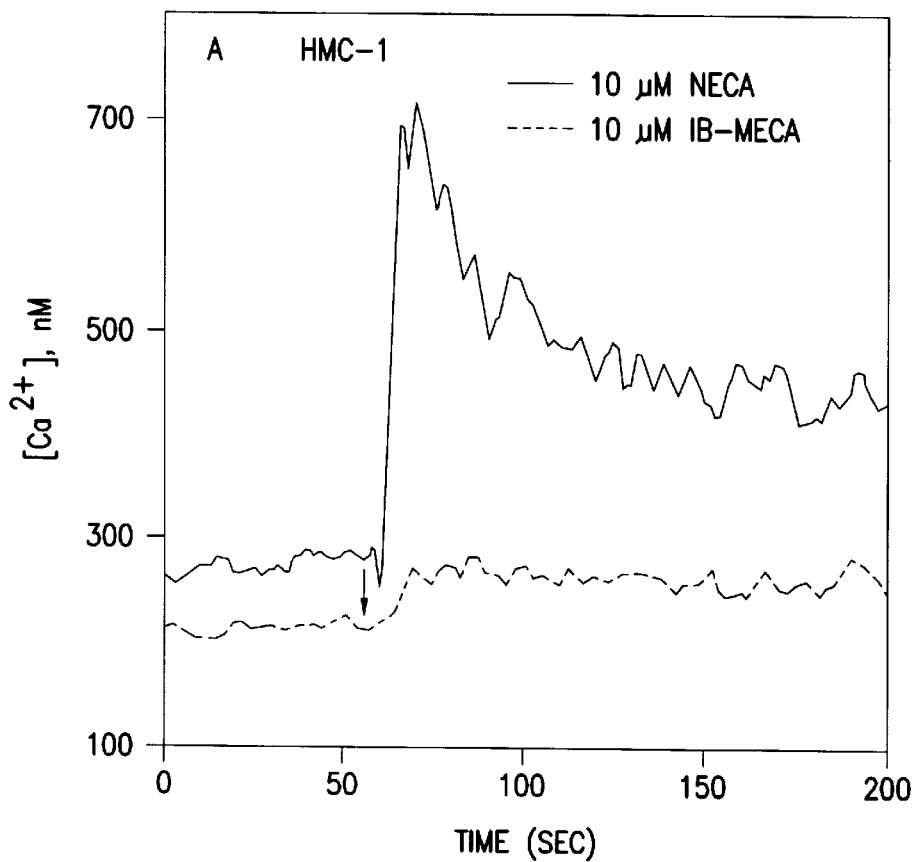
FIGS. 1A and 1B illustrate that 5-N-ethylcarboxamidoadenosine (NECA) but not $N^6$-(2-iodo)benzyl-5'-N-methylcarboxamidoadenosine (IB-MECA) stimulates human mast cells to mobilize calcium and to accumulate cyclic AMP.

The present invention relates to a method for achieving a blockade of the mast cell degradation response induced through adenosine activation of the A2B adenosine receptor subtype. The method comprises contacting cells bearing the A2B receptor with an amount of an adenosine A2B receptor subtype specific inhibitor comprising an 8-phenyl or 8-cycloalkyl substituted xanthine or 8-substituted xanthine derivative effective to block activation of the receptor by adenosine.

Further, the invention relates to a method for treating or preventing myocardial ischemia, inflammation, brain arteriole diameter constriction, and/or the release of allergic mediators. The method comprises using a specific inhibitor of the A2B adenosine receptor subtype to inhibit effects induced by adenosine mediated mast cell degranulation by contacting A2B receptor bearing mast cells with an amount of a selective A2B inhibitor comprising an 8-phenyl or 8-cycloalkyl substituted xanthine or 8- substituted xanthine derivative effective to prevent mast cell degranulation.

Further the invention relates to a method for preventing or treating asthma, bronchoconstriction, allergic potentiation, inflammation or reperfilsion injury in a human. The method comprises administering to the human an effective amount of an adenosine A2B receptor specific inhibitor comprising an 8-phenyl or 8-cycloalkyl substituted xanthine or substituted xanthine derivative to antagonize activation of the adenosine receptor of the A2B subtype by adenosine.

Further, the invention relates to a method for preventing mast cell degranulation in a human. The method comprises administering to the human an amount of an adenosine A2B receptor specific inhibitor comprising an 8-substituted xanthine or 8- substituted xanthine derivative effective to antagonize activation of the adenosine receptor of the A2B subtype by adenosine.

Further, the invention relates to a method for treating an autoimmune disease selected from the group consisting of Addison's disease (adrenal), autoimmune hemolytic anemia (red cells), Crohn's disease (gut), Goodpasture's syndrome (kidney and lungs), Grave's disease (thyroid), Hashimoto's thyroiditis (thyroid), idiopathic thrombocytopinic purpura (platelets), Insulin-dependent diabetes militus (pancreatic beta cells), multiple sclerosis (brain and spinal cord), myasthenia gravis (nerve/muscle synapses), *Pemphigus vulgaris* (skin), pernicious anemia (gastric parietal cells), poststreptococcal glomerulonephritis (kidney), psoriasis (skin), rheumatoid arthritis'(connective tissue), scleroderma (heart, lung, gut, kidney), Sjogren's syndrome (liver, kidney, brain, thyroid, salivary gland), spontaneous infertility (sperm), and systemic lupus erythematosus (DNA, platelets, other tissues). The method comprises administration to a patient in need thereof of an effective amount of a selective A2B adenosine receptor antagonist comprising an 8- substituted xanthine or 8-substituted xanthine derivative to inhibit mast cell degranulation.

Further, the invention relates to a method for the treatment or prevention of disease states mediated through activation of the A2B subtype of the adenosine receptor on mast cells by prevention of mast cell degranulation through blockade of the A2B subtype of the adenosine receptor. The method comprises contacting mast cells with an inhibitory effective amount of an adenosine A2B receptor specific inhibitor comprising an 8- substituted xanthine or 8-substituted xanthine derivative specific for the A2B receptor subtype. The disease state includes asthma, myocardial reperfusion injury, allergic reactions including but not limited to rhinitis, poison ivy induced responses, urticaria, scleroderma, arthritis, and inflammatory bowel diseases.

A preferred 8-phenyl or 8-cycloalkyl substituted xantine or 8- substituted xanthine derivative has the formula:

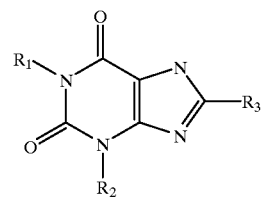

wherein $R_1$ is a hydrogen, an alkyl, a cycloalkyl, or an aryl; $R_2$ is a cycloalkyl or an aryl; and $R_3$ is a phenyl, substituted phenyl, cycloalkyl or substituted cycloalkyl. Specifically, when the 8-phenyl substituted xanthine or 8-phenyl substituted xanthine derivative is BW 493,

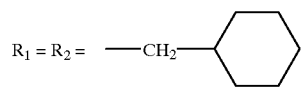

and $R_3$ is

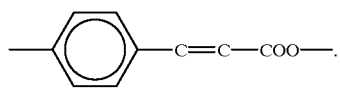

When enprofylline is selected as the 8-phenyl substituted xanthine or 8-phenyl substituted xanthine derivative, $R_1$=H, $R_2$=C—C—C and $R_3$=H.

Preferably the 8-phenyl or 8-cycloalkyl substituted xanthine or 8-substituted xanthine derivative has an affinity for the A2B subtype of the human adenosine receptor which is at least one order of magnitude greater than the affinity for either the A1 or A2 subtypes of the human adenosine receptor effective to antagonize activation of the adenosine receptor of the A2B subtype by adenosine when:

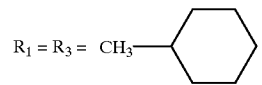

More preferably, the 8-phenyl or 8-cycloalkyl substituted xanthine or 8-substituted xanthine derivative has a pKi for the A2B subtype of 7 or greater and a pKi for other adenosine receptor subtypes of 6 or less. Most preferably, the 8-phenyl or 8-cycloalkyl substituted xanthine or 8- substituted xanthine derivative is BW 493.

The following examples are provided to further define but not to limit the invention defined by the foregoing description and the claims which follow:

EXAMPLE 1

Functional Responses Of Human HMC-1 Mast Cells to NECA and IB-MECA

In tests as described in "Canine Mast Cell Adenosine Receptors: Cloning and Expression of the A3 Receptor and Evidence that Degranulation is Mediated by the A2B Receptor," *Molecular Pharmacology*, 52:1–15 (1997) to, Auchampapch et al., that reference being incorporated herein by reference, intact cells were treated with the A3-selective agonist IB-MECA and the nonselective agonist NECA.

Figure 1B:
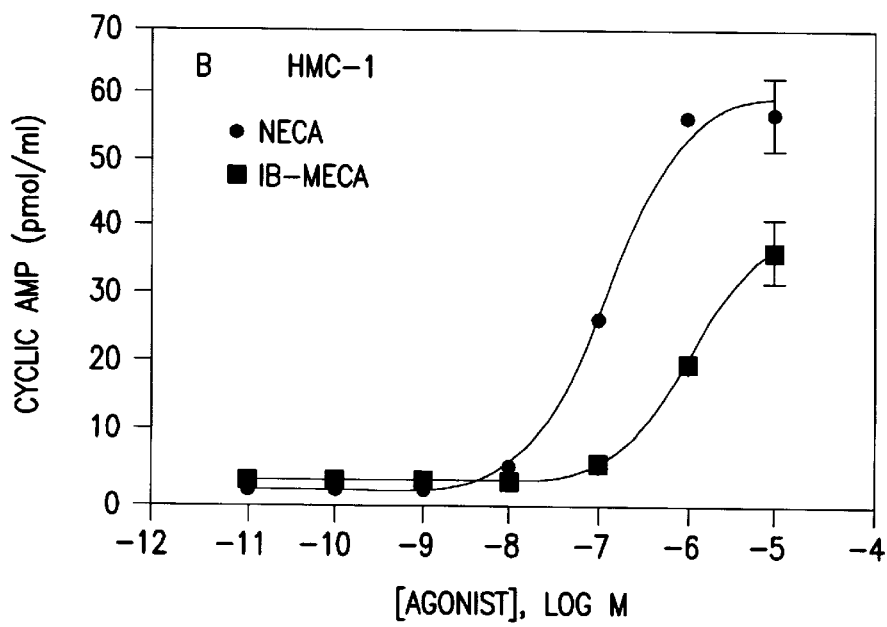

FIGS. 1A and 1B show (A) Intracellular $Ca^{2+}$ accumulation measured in cells pretreated with the $Ca^{2+}$-sensitive fluorescent reporter, FURA and (B) Cyclic AMP accumulation measured by radioimmunoassay. The results are typical of triplicate experiments. FIGS. 1A and 1B show that NECA, but not IB-MECA stimulates canine mast cells to mobilize calcium and to accumulate cyclic AMP. Agonists of A1 or A2A adenosine receptors do not have these effects. These data suggest that canine mast cells are activated by A2B rather than A3 adenosine receptors.

EXAMPLE 2

Binding of Enprophylline and Theophylline to Human Adenosine Receptors

Figure 7:
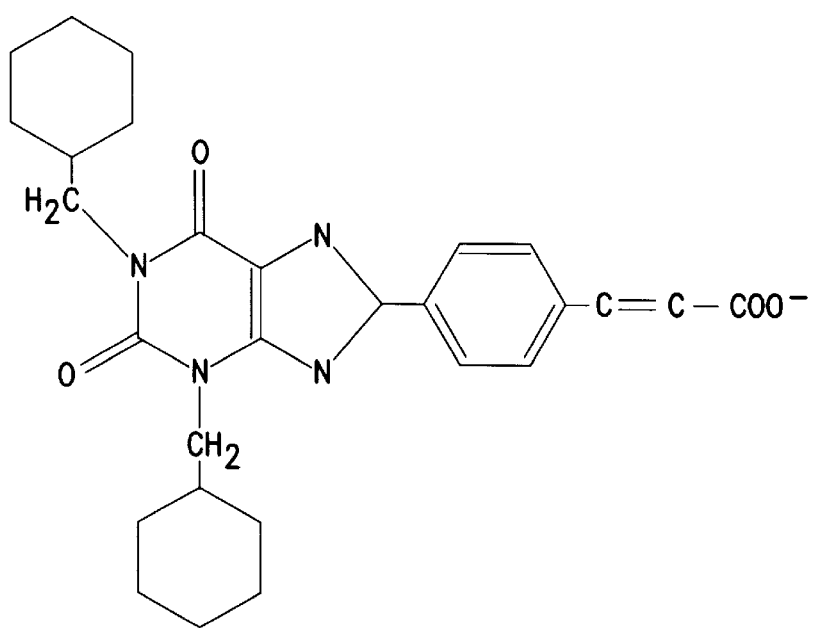
FIG. 7 is an illustration of structures to further identify compounds described in this application.

The xanthines theophylline and enprofylline (See FIG. 7) are used clinically to treat asthma. However, enprofylline has been reported to bind weakly to adenosine receptors. Lunell et al., Effects of enprofylline, a xanthine lacking adenosine receptor antagonism, in patients with chronic obstructive lung disease, *European Journal of Clinical Pharmacoloy* 22:395–402 (1982).

Competition for specific radioligand binding of enprophylline and theophylline was measured on membranes prepared from cells expressing (A) recombinant human A2B adenosine receptors and (B) recombinant human A3 adenosine receptors as described in "Molecular Characterization of Recombinant Human Adenosine Receptors," *Drug Development Research*, 39:243–252 (1996) to Robeva et al., which is incorporated herein by reference.

Figure 2A:
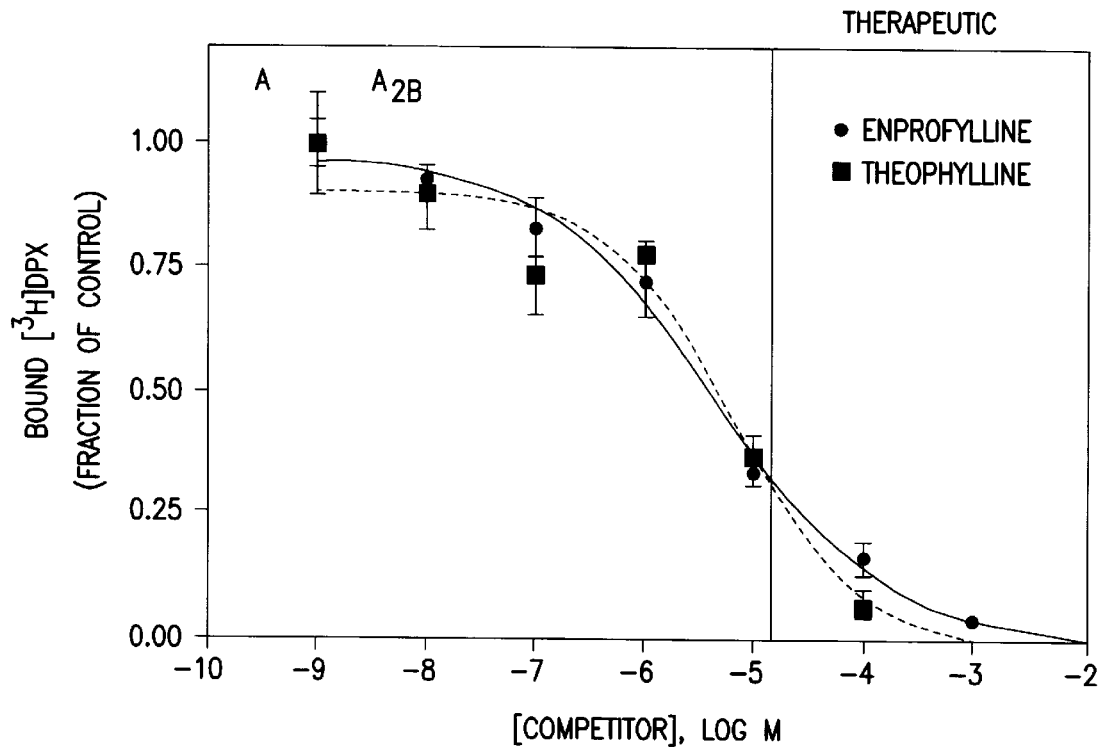
FIG. 2A is an illustration of competitive binding studies of theophylline and enprofylline for the rhA2B adenosine receptor.
Figure 2B:
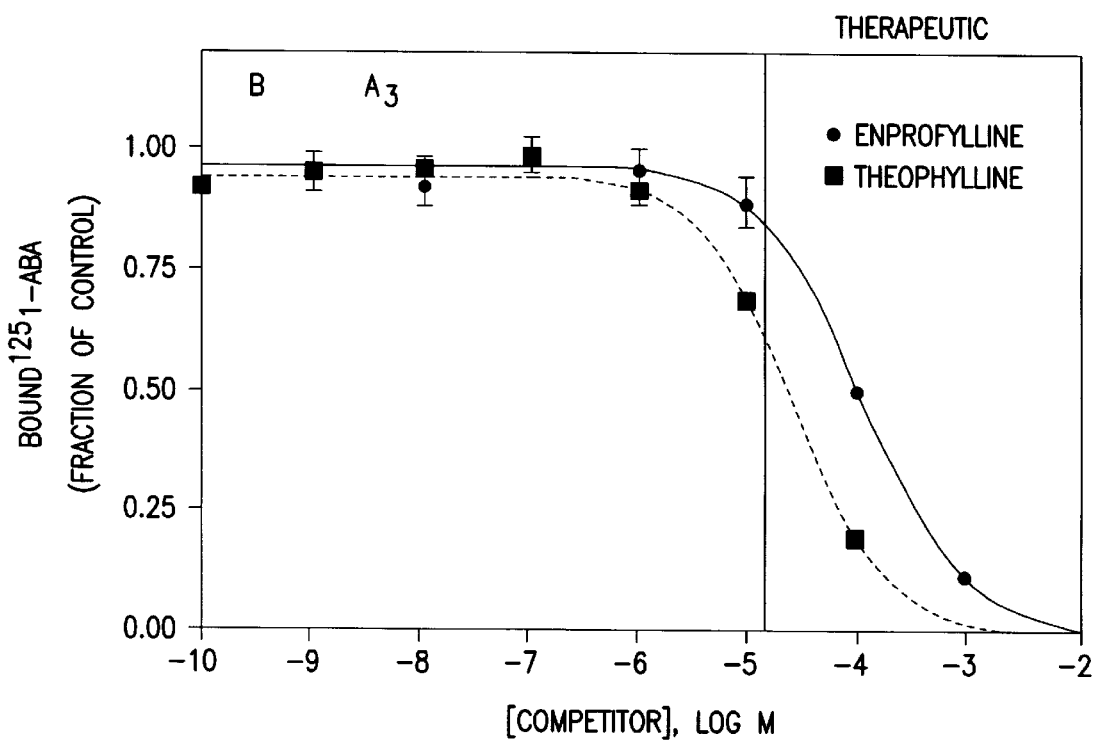
FIG. 2B is an illustration of competitive binding studies of theophylline and enprofylline for the rhA3 adenosine receptor.

As shown in FIGS. 2A and 2B, each point is the mean standard error of the mean (SEM) of triplicate determinations. The results are typical of three experiments. In the competition binding studies shown, theophylline and enprofylline compete for [$^3$H]1,3-diethyl-8-phenylxanthine ([$^3$H]DPX, 5 nM) binding to rhA2B adenosine receptors as shown in FIG. 2A. Both antagonist have higher affinities for human A2B adenosine receptors than for human A3 adenosine receptors (see FIG. 2B) with A2B $K_i$ values of 7.1 $\mu$M and 5.6 $\mu$M for theophylline and enprofylline, respectively.

EXAMPLE 3

Functional Antagonism by Enprofylline and Theophylline of Recombinant A2B Receptor-Mediated Cyclic AMP Accumulation Agonists were used to modulate cAMP in HEK 293 cells stably transfected the rhA2B adenosine receptors or rhA3 adenosine receptors. This procedure is also described in the Auchampach et al. publication.

Figure 3A:
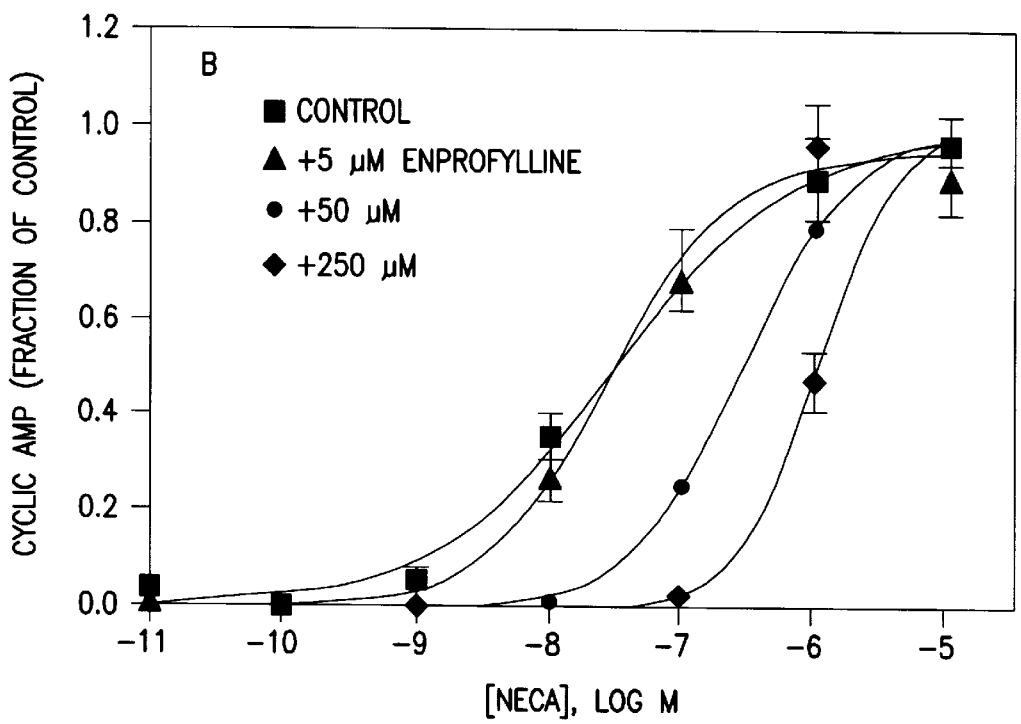
FIGS. 3A and 3B illustrate the functional effects of theophylline and enprofylline in modulating cAMP in HEK 293 cells transfected with A2B adenosine receptor cells.
Figure 3B:
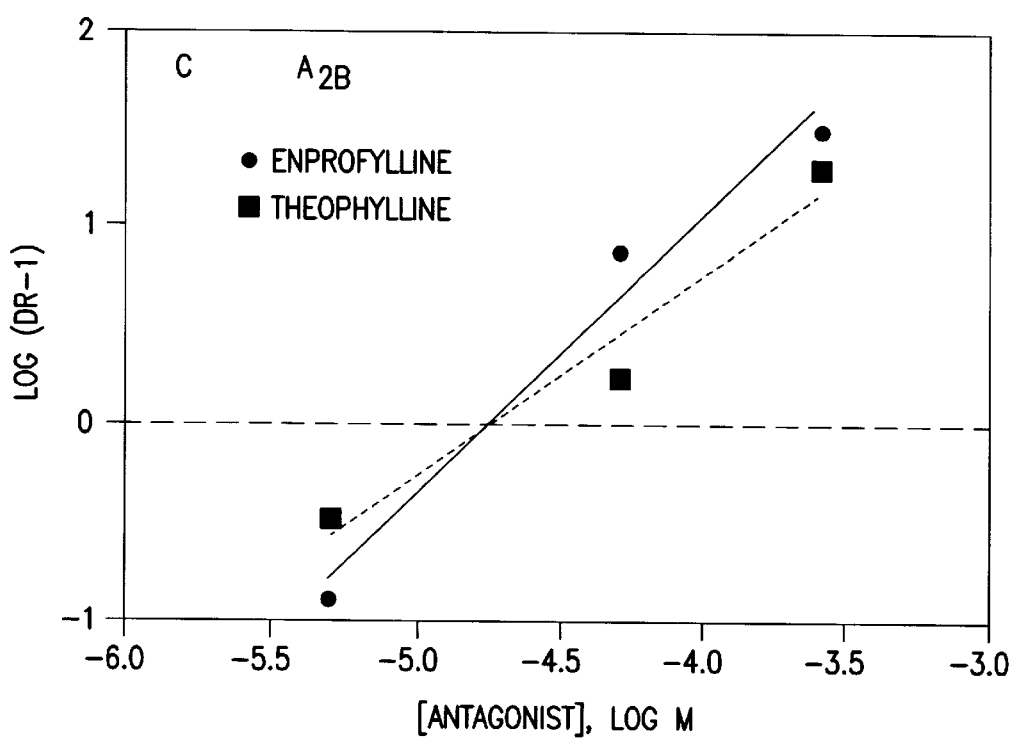

FIGS. 3A and 3B shows antagonists of NECA-stimulated cyclic AMP accumulation in transfected HEK-293 cells by (A) theophylline and (B) enprofylline. Line (C) is Schild analysis of the data shown in (A) and (B).

NECA or IB-MECA produced a dose-dependent functional response in cells expressing rhA2B adenosine receptors or rhA3 adenosine receptors respectively. The addition of theophylline or enprofylline produced a progressive shift to the right in the potency of NECA in these functional assays. Schild analyses of the data gave A2B $K_i$ values of 16.7 $\mu$M for theophylline and 17.1 $\mu$M for enprofylline.

For rhA3 adenosine receptors, the A3-selective agonist, IB-NECA was used to generate dose-response curves for inhibition of isoproferenol-stimulated cyclic accumulation in the absence or presence of different concentrations of theophylline or enprofylline. IB-MECA produced dose-dependent inhibition of cAMP accumulation stimulated by 1 $\mu$M isoproterenol; the maximum inhibition was 50–70%.

Figure 4:
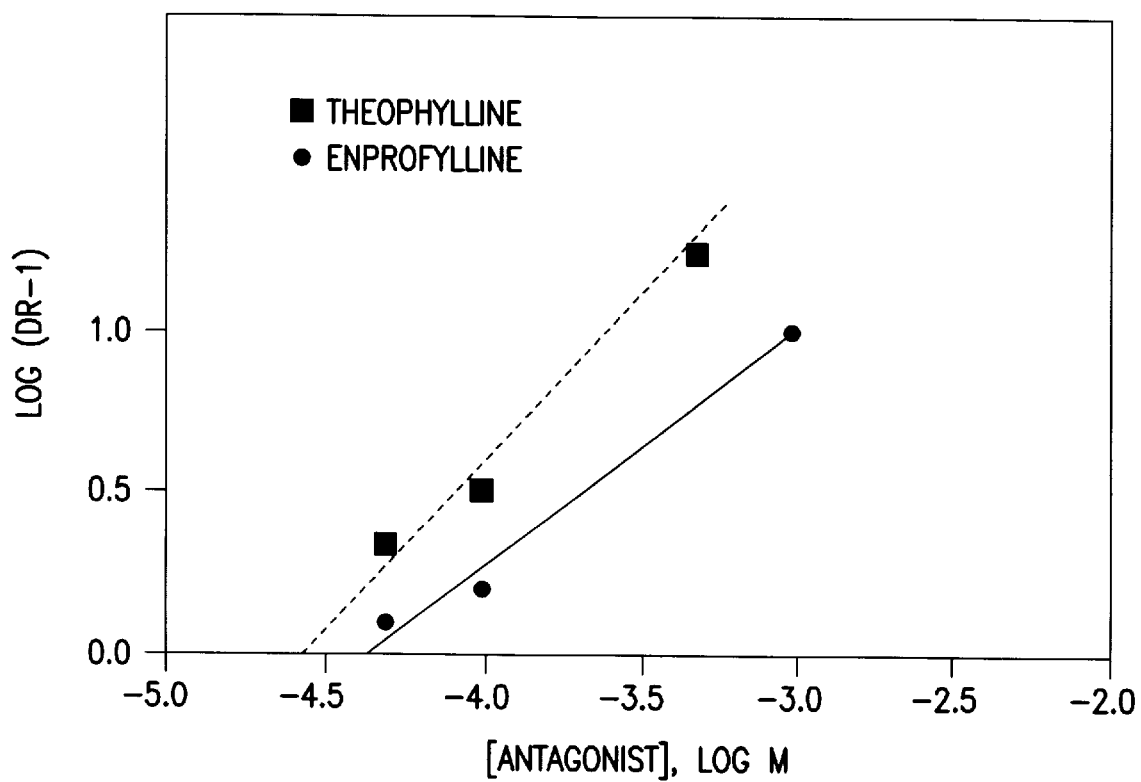
FIG. 4 is an illustration of the functional effects of theophylline and enprofylline in modulating cAMPin HEK 293 cells transfected with A3 adenosine receptor cells.

The presence of increasing concentrations of either theophylline or enprofylline shifted the dose-response curve progressively to the right, with $K_i$ values of 27.6 $\mu$M for theophylline and 39.6 $\mu$M for enprofylline based on Schild analysis (see FIG. 4). For both A2B and A3 receptors, the $K_i$ values of theophylline and enprofylline obtained from cAMP functions assays are in good agreement with the $K_i$ values calculated from radioligand competition binding assays.

EXAMPLE 4

Effect of Theophylline and Enprofylline of IP$_3$ Generation

On agonist stimulation, A2B adenosine receptors activate phospholipase C leading to inositol-(1,4,5)-trisphosphate (IP$_3$) formation, Characteristically, A2B-mediated effects are insensitive to blockage by pertussis toxin.

In this example, untransfected HEK-293 (HEK 293) or cells transfected with recombinant human A2B adenosine receptors were treated with the indicated compounds. IP$_3$ was measured in cells pretreated with [$^3$H]inositol. This procedure is also described in the Auchampach et al. publication.

Figure 5:
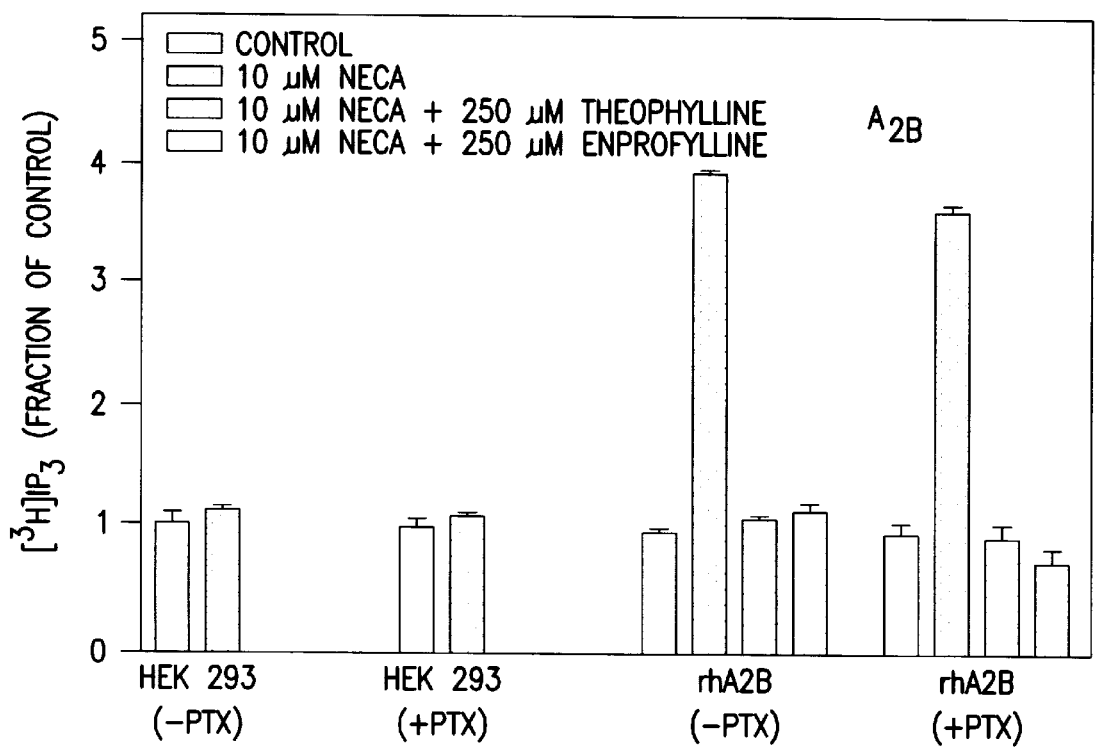
FIG. 5 is an illustration of the effects of theophylline and enprofylline on inositol-(1,4,5)-trisphosphate ($IP_3$) generation.

As shown in FIG. 5, NECA at 10 $\mu$M produced a 3.5 fold increase in IP$_3$ formation in rhA2B adenosine receptor transfected HEK 293 cells. At 250 $\mu$M, both theophylline and enprofylline were able to block the increase in IP$_3$ produced by 10 $\mu$M NECA in human A2B adenosine receptor transfected HEK 293 cells. Neither antagonist affected basal levels of inositol phosphates.

EXAMPLE 5

Effect of Theophylline and Enprofylline on the Ca$^{2+}$ Mobilization

The activation of the phospholipase C pathway leads to intracellular calcium mobilization. NECA produces a dose-dependent increase in intracellular Ca$^{2+}$ content in human A2B adenosine receptor transfected cells.

Figure 6:
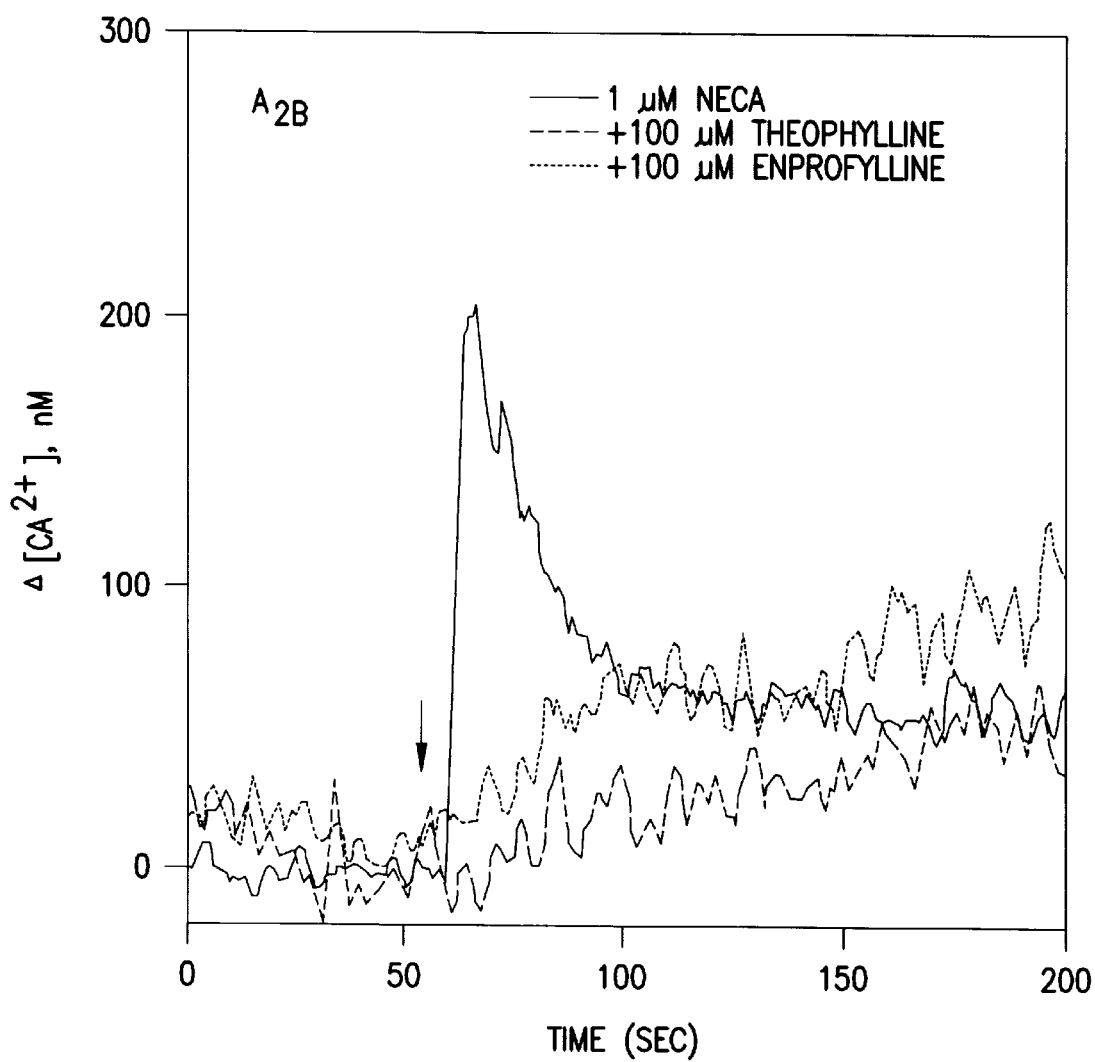
FIG. 6 is an illustration of the effects of theophylline and enprofylline on intracellular calcium mobilization.

HEK-293 cells transfected with recombinant human A2B adenosine receptors were treated with the compounds indicated in FIG. 6. Calcium mobilization was measured in cells preloaded with FURA. Again, this procedure is also described in the Auchampach et al. publication.

As shown in FIG. 6, theophylline or enprofylline at 100 $\mu$M totally blocks the Ca$^{2+}$ response induced by 1 $\mu$M NECA.

EXAMPLE 6

Screening to Identify Selective Antagonists of Recombinant Human A2B Adenosine Receptors A series of compounds was screened to identify potent A2B selective antagonists. This was done in competition binding assays using recombinant human A1, A2A, A2B or A3 adenosine receptors, similar to that illustrated in FIGS. 2A and 2B.

TABLE 1

The following $K_i$ values (nM) show that BW-A493 is a potent and selective A2B antagonist:

|     | BW-A493       | Enprofylline        |
| --- | ------------- | ------------------- |
| A1  | 4980 ± 553    | 156,000 ± 109,000   |
| A2A | 1518 ± 797    | 32,000 ± 7,800      |
| A2B | 198 ± 52      | 7,000 ± 1,850       |
| A3  | 922 ± 399     | 65,000 ± 12,100     |

One should note that the lowest $K_i$ value corresponds to the highest affinity; BW-A493 and enprofylline are A2B selective. As shown above, BW-A493 is approximately 35 times more potent than enprofylline as an antagonist of human A2B adenosine receptors.

Examples 1 to 5 indicate that known anti-inflammatory compounds are antagonists of A2B. The Examples establish that enprofylline, a compound used to treat asthma, but which previously had an unknown mechanism of action, blocks human A2B adenosine receptors and that human HMC-1 mast cells have A2B receptors indicating that antagonists of A2B as well as A3 adenosine receptors have anti-inflammatory action. Example 6 identifies BW-A493 as a selective antagonist of human A2B adenosine receptors.

Enprofylline can be used in moderately severe asthmatic patients. Typically, a bolus injection of 1.5 mg/kg enprofylline is given over 20 minutes and then a maintenance infusion of 0.4 mg/kg/h is given for up to 24 hours.

While the foregoing specification teaches the principles of the present invention, with examples provided for the purpose of illustration, it will be understood that the practice of the invention encompasses all of the variations, adaptations, modifications as come within the scope of the following claims and their equivalents.

What is claimed is:

1. A method for preventing or treating asthma, bronchoconstriction, allergic potentiation, inflammation or reperfusion injury in a human in need thereof which comprises administering an effective amount of an adenosine A2B receptor specific inhibitor comprising an 8-cycloalkyl or 8-substituted-cycloalkyl substituted xanthine.

2. The method of claim 1 wherein said xanthine has the formula:

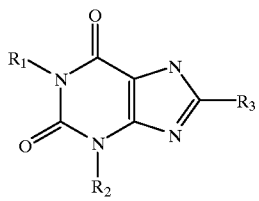

wherein said $R_1$ is a hydrogen, an alkyl, a cycloalkyl, or an aryl; $R_2$ is a cycloalkyl or an aryl; and $R_3$ is cycloalkyl or a substituted cycloalkyl.

3. The method of claim 1 wherein said xanthine is a 1-propyl xanthine.

4. The method of claim 1 wherein said xanthine has the formula:

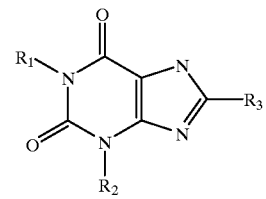

wherein $R_1$ and $R_2$ are each cyclohexylmethyl; and $R_3$ is cycloalkyl.

5. The method of claim 1 wherein said xanthine has an affinity for the A2B subtype of the human adenosine receptor which is at least one order of magnitude greater than the affinity for either the A1 or A2A subtypes of the human adenosine receptor.

6. The method of claim 1 wherein said xanthine has a pKi for the A2B subtype of 7 or greater and a pKi for other adenosine receptor subtypes of 6 or less.

7. A method for preventing mast cell degranulation in a human in need thereof which comprises administering an effective amount of adenosine A2B receptor specific inhibitor comprising an 8-cycloalkyl or 8-substituted-cycloalkyl xanthine.

8. The method of claim 7 wherein said xanthine has the formula:

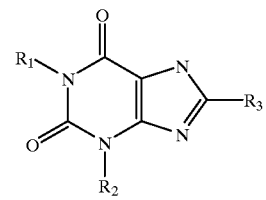

wherein said $R_1$ is a hydrogen, an alkyl, a cycloalkyl, or an aryl; $R_2$ is a cycloalkyl or an aryl; and $R_3$ is cycloalkyl or a substituted cycloalkyl.

9. The method of claim 7 wherein said xanthine is a 1-propyl xanthine.

10. The method of claim 7 wherein said xanthine has the formula:

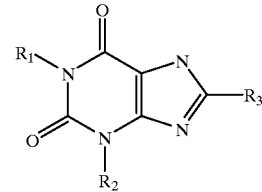

wherein $R_1$ and $R_2$ are each cyclohexylmethyl; and $R_3$ is cycloalkyl.

11. The method of claim 7 wherein said xanthine has an affinity for the A2B subtype of the human adenosine receptor which is at least one order of magnitude greater than the affinity for either the A1 or A2A subtypes of the human adenosine receptor.

12. The method of claim 7 wherein said xanthine has a pKi for the A2B subtype of 7 or greater and a pKi for other adenosine receptor subtypes of 6 or less.

* * * * *

UNITED STATES PATENT AND TRADEMARK OFFICE
CERTIFICATE OF CORRECTION

PATENT NO. : 6,117,878
DATED : September 12, 2000
INVENTOR(S) : Linden

It is certified that error appears in the above-identified patent and that said Letters Patent is hereby corrected as shown below:

<u>Column 1</u>,
After the title "8-PHENYL– OR 8-CYCLOALKYL XANTHINE ANTAGONISTS OF A2B HUMAN ADENOSINE RECEPTORS" and before "BACKGROUND OF THE INVENTION", insert -- This invention was made with Government support under Grant No. HL37942, awarded by the National Institute of Health (NIH). The Government has certain rights in this invention --.

Signed and Sealed this

Thirteenth Day of November, 2001

Attest:

*Nicholas P. Godici*

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO. : 6,117,878
DATED : September 12, 2000
INVENTOR(S) : Linden

It is certified that error appears in the above-identified patent and that said Letters Patent is hereby corrected as shown below:

Title page,
Item [73], Assignees, should read -- University of Virginia Patent Foundation, Charlottesville, VA. --.

Signed and Sealed this

Twenty-first Day of February, 2006

JON W. DUDAS
*Director of the United States Patent and Trademark Office*